United States Patent [19]

Grue-Sørensen

[11] Patent Number: 5,716,945
[45] Date of Patent: Feb. 10, 1998

[54] VITAMIN D ANALOGUES

[75] Inventor: Gunnar Grue-Sørensen, Ølstykke, Denmark

[73] Assignee: Leo Pharmaceutical Products Ltd. A/S (Løvens Kemiske Fabrik Produktionsaktieselskab), Ballerup, Denmark

[21] Appl. No.: 545,762

[22] PCT Filed: Jul. 1, 1994

[86] PCT No.: PCT/DK94/00271

§ 371 Date: Nov. 7, 1995

§ 102(e) Date: Nov. 7, 1995

[87] PCT Pub. No.: WO95/02577

PCT Pub. Date: Jan. 26, 1995

[30] Foreign Application Priority Data

Jul. 12, 1993 [GB] United Kingdom ............... 9314400

[51] Int. Cl.$^6$ .................. A01N 45/00; C07C 401/00; C07C 35/21; C07C 35/22
[52] U.S. Cl. .................. 514/167; 552/653; 568/816; 568/817
[58] Field of Search ............... 514/167; 552/653; 568/816, 817

[56] References Cited

U.S. PATENT DOCUMENTS

| | | |
|---|---|---|
| 5,145,846 | 9/1992 | Baggiolini . |
| 5,206,229 | 4/1993 | Calverley . |
| 5,378,695 | 1/1995 | Calverley . |
| 5,449,668 | 9/1995 | Sestelo . |

FOREIGN PATENT DOCUMENTS

| | | |
|---|---|---|
| 326 875 | 8/1989 | European Pat. Off. . |
| 91 00855 | 1/1991 | WIPO . |

Primary Examiner—Gary Geist
Assistant Examiner—Karl J. Puttlitz, Jr.
Attorney, Agent, or Firm—Cushman Darby & Cushman IP Group Pillsbury Madison & Sutro LLP

[57] ABSTRACT

The present invention relates to compounds of formula in which formula X is hydrogen or hydroxy; $R^1$ and $R^2$, which may be the same or different, stand for hydrogen or $C_1$–$C_4$ hydrocarbyl; or $R^1$ and $R^2$, taken together with the carbon atom bearing the group X, can form a $C_3$–$C_8$ carbocyclic ring; Q is a single bond or a $C_1$–$C_4$ hydrocarbylene diradical; $R^1$, $R^2$ and/or Q may be optionally substituted with one or more fluorine atoms; and prodrugs of formula in which one or more of the hydroxy groups are masked as groups which can be reconverted to hydroxy groups in vivo. The compounds show antiinflammatory and immunomodulating effects as well as stong activity in inducing differentiation and inhibiting undesirable proliferation of certain cells.

9 Claims, No Drawings

VITAMIN D ANALOGUES

This application claims benefit of international application PCT/DK94/00271 filed Jul. 1, 1994.

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, of a number of disease states including diabetes mellitus, hypertension, acne, alopecia, skin ageing, imbalance in the immune system, of inflammatory diseases such as rheumatoid arthritis and asthma, of diseases characterized by abnormal cell differentiation and/or cell proliferation such as e.g. psoriasis and cancer, for prevention and/or treatment of steroid induced skin atrophy, and for promoting osteogenesis and treating osteoporosis.

The compounds of the present invention are represented by the general formula I

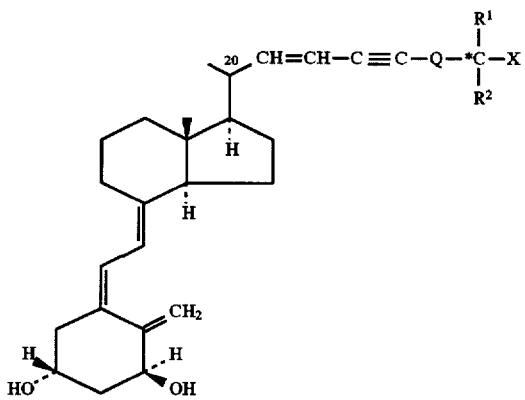

in which formula X is hydrogen or hydroxy; $R^1$ and $R^2$ which may be the same or different, stand for hydrogen or $C_1-C_4$ hydrocarbyl; or $R^1$ and $R^2$ taken together with the carbon atom bearing the group X, can form a $C_3-C_8$ carbocyclic ring; Q is a single bond or a $C_1-C_4$ hydrocarbylene diradical; $R^1$, $R^2$ and/or Q may be optionally substituted with one or more fluorine atoms.

In the context of this invention, the expression hydrocarbyl radical (hydrocarbylene diradical) indicates the residue after removal of 1 (2) hydrogen atom(s) from a straight, branched or cyclic, saturated or unsaturated hydrocarbon.

Examples of $R^1$ and $R^2$ when taken separately include, but are not limited to, hydrogen, methyl, trifluoromethyl, ethyl, vinyl, normal-, iso- and cyclopropyl and propen-2-yl.

Examples of $R^1$ and $R^2$ when taken together include ethylene, tri-, tetra- and pentamethylene.

Examples of Q include, but are not limited to, a single bond, methylene, ethylene, trimethylene, dimethylmethylene, CH=CH, C≡C, $CH_2CH$=CH and $CH_2$—C≡C.

The compounds of the invention comprise more than one diastereoisomeric form (e.g., R or S configuration at C-20 and, if $R^1$ and $R^2$ are different, at the starred carbon atom; E or Z configuration at the 22,23 double bond and E or Z configuration when a double bond is present in the group Q). The invention covers all these diastereoisomers in pure form and also mixtures thereof. In addition, prodrugs of I in which one or more of the hydroxy groups are masked as groups which can be reconverted to hydroxy groups in vivo are also within the scope of the invention.

The compounds I in which X is hydroxy are the preferred ones, but the compounds I in which X is hydrogen are actually another type of prodrug. These compounds are relatively inactive in vitro, but are converted to active compounds of formula I, where X=OH, by enzymatic side chain hydroxylation after administration to the patient.

It has been shown that $1\alpha,25$-dihydroxy-vitamin $D_3$ (1,25 $(OH)_2D_3$) influences the effects and/or production of interleukins (Muller, K. et al., Immunol. Lett. 17, 361–366 (1988)), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma.

It has also been shown that $1,25(OH)_2D_3$ is able to stimulate the differentiation of cells and inhibit excessive cell proliferation (Abe, E. et al., Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of $1,25(OH)_2D_3$, or its pro-drug $1\alpha$-OH-$D_3$, for the treatment of hypertension (Lind, L. et at., Acta Med. Scand. 222, 423–427 (1987)) and diabetes mellitus (Inomata, S. et al., Bone Mineral 1, 187–192 (1986)) has been suggested. Another indication for $1,25(OH)_2D_3$ is suggested by the recent observation of an association between hereditary vitamin D resistance and alopecia: treatment with $1,25(OH)_2D_3$ may promote hair growth (Editorial, Lancet, March 4, p. 478 (1989)). Also, the fact that topical application of $1,25(OH)_2D_3$ reduces the size of sebaceous glands in the ears of male Syrian hamsters suggests that this compound might be useful for the treatment of acne (Malloy, V. L. et al., the Tricontinental Meeting for Investigative Dermatology, Washington, (1989)).

However, the therapeutic possibilities in such indications of $1,25(OH)_2D_3$ are severely limited by the well known potent effect of this hormone on calcium metabolism; elevated blood concentrations will rapidly give rise to hypercalcemia. Thus, this compound and some of its potent synthetic analogues are not completely satisfactory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

The vitamin D analogue calcipotriol (INN) or calcipotriene (USAN) is recognized worldwide as a safe and efficient drug in the treatment of psoriasis.

A recent study (Colston, K. W. et al., Biochem. Pharmacol. 44, 693–702 (1992)) support the concept that vitamin D derivatives may inhibit breast cancer cell proliferation in vivo. Promising immunological properties of vitamin D analogues have been described (Binderup, L. Biochem. Pharmacol. 43, 1885–1892 (1992)).

Analogues of vitamin $D_3$ with conjugated unsaturation in the side chain have been described (PCT publication number WO 91/00855) (Binderup, E. et al. in Vitamin D, Gene Regulation, Structure-Function Analysis and Clinical Application, ed. by Norman, A. W., Bouillon, R. and Thomasset, M., Walter de Gruyter, Berlin, (1991), 192–193). In particular, EB1089 (1(S),3(R)-Dihydroxy-20(R)-(5'-ethyl-5'-hydroxy-hepta-1' (E),3'(E)-dien-1'-yl)-9,10-secopregna-5(Z),7(E), 10(19)-triene), an analogue of calcitriol with a conjugated diene side chain, has been the subject for intensive studies towards the development of anti-cancer agents (cf. Abstracts from Ninth Workshop on Vitamin D, May 28–Jun. 2, 1994, Orlando, Fla., USA).

The fact that only small structural differences between analogues of vitamin D may give large variation in their biological activities (cf. Binderup, L. et al., Biochem. Pharmacol. 42, 1569–1575 (1991)) implies that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the fact that receptor binding affinities in vitro do not always follow those found by in vivo studies, probably reflecting a pharmacokinetic difference between the compounds.

The compounds of the present invention are 22-ene-24-yne-analogues of vitamin D and differ structurally from any known vitamin D analogues. Both analogues with the 20S and the 20R configuration are prepared by the methods of this invention. These compounds are highly active and show favourable selectivity. Thus, a particular compound of formula I is observed to show one or more of the following advantages when comparison to prior art is made:

(a) more potent effects on cell differentiation/proliferation;
(b) a greater selectivity in favour of the potent effects on cell differentiation/proliferation contra the effects on calcium metabolism;
(c) greater stability in acid (of importance by the oral administration route).

In the Scheme below, data from the testing of compounds of this invention and of prior art compounds calcipotriol (see above) and EB1089 (see above) are shown:

| Compound | U937, inhib. of prolifer.[a] | Calcium metabolism[b] | Acid stability[c] |
|---|---|---|---|
| 101 | 89 | 0.2 | not determined |
| 102 | 1.1 | 0.015 | 15–30 min |
| Calcipotriol | 1 | 0.005 | |
| EB1089 | 68 | 0.4 | <5 min |

[a]This test determines the antiproliferative effect in U937 human histiocytic leukemia cells of the compound relative to 1α,25(OH)$_2$ D$_3$. A number greater than 1 indicates a higher antiproliferative activity of the compound in question when compared to 1α,25(OH)$_2$ D$_3$. The test was performed exactly as described: L. Binderup and E. Bramm, Biochem. Pharmacol., 37, (1988) 889–895.
[b]This test determines the calciuric effect in rats of the compound relative to 1α,25(OH)$_2$ D$_3$. A number smaller than 1 indicates less change in calcium excretion of the compound in question when compared to 1α,25(OH)$_2$ D$_3$. The test was, as above, performed exactly as described: L. Binderup and E. Bramm, Biochem. Pharmacol., 37, (1988) 889–895.
[c]In this test, the compound was treated with a mixture of 10 μl conc. $^2$HCl/$^2$H$_2$O in C$^2$H$_3$CN (0.6 ml) at 25° C. and the approximate half life was determined by $^1$H NMR at 500 MHz.

It appears from the Table that the ratio between the desired antiproliferative and the undesired calcemic activity is higher for compound 101 than for both calcipotriol and EB1089.

The compounds of the invention are therefore especially suited for both local and systemic treatment and prophylaxis of human and veterinary disorders which are characterized by abnormal cell proliferation and/or cell differentiation, such as certain dermatological disorders including psoriasis and certain cancer forms, and/or by an imbalance in the immune system, e.g. in autoimmune diseases, including diabetes mellitus, host versus graft reaction, and rejection of transplants. The compounds of the invention are also suited for the treatment of inflammatory diseases, such as rheumatoid arthritis and asthma. Acne, alopecia, and hypertension are other conditions which may be treated with the compounds of the invention. Finally, as thickening of the skin is observed after topical treatment with the compounds of the invention, these compounds may be useful for treatment or prevention of skin atrophy and skin ageing, including photoageing.

Because of the low tendency of the compounds to produce hypercalcemia on continued administration they are expected to be valuable for the long term treatment of hyperparathyroidism (particularly secondary hyperparathyroidism associated with renal failure) and for promoting osteogenesis and treating osteoporosis.

The present compounds, may be used in combination with other pharmaceuticals. In the prevention of graft rejection and graft versus host reaction, a treatment with the present compounds may advantageously be combined with cyclosporin A treatment.

The compounds of formula I may conveniently be prepared from the vitamin D derivatives 1 or 2 by the routes outlined in Scheme 1.

The following standard abbreviations are used throughout this disclosure: DMF=N,N-dimethylformamide; Et=ethyl; "HF"=5% hydrogen fluoride in acetonitrile:water (7:1, v/v); Me=methyl; pet.ether=petroleum ether (mainly pentate); PPTS=pyridinium toluene-4-sulfonate; r.t.=room temperature; TBAF=tetra-n-butylammonium fluoride trihydrate; TBDMS=tert-butyldimethylsilyl; THF=tetrahydrofuran; THP=tetrahydro-4H-pyran-2-yl; TMS=trimethylsilyl; TsO=toluene-4-sulfonate.

Scheme 1
Synthesis of the Compound of Formula I

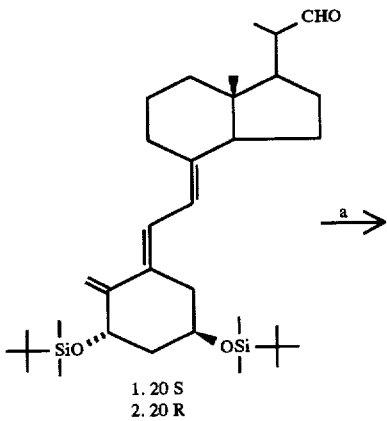

1. 20 S
2. 20 R

Scheme 1
Synthesis of the Compound of Formula I

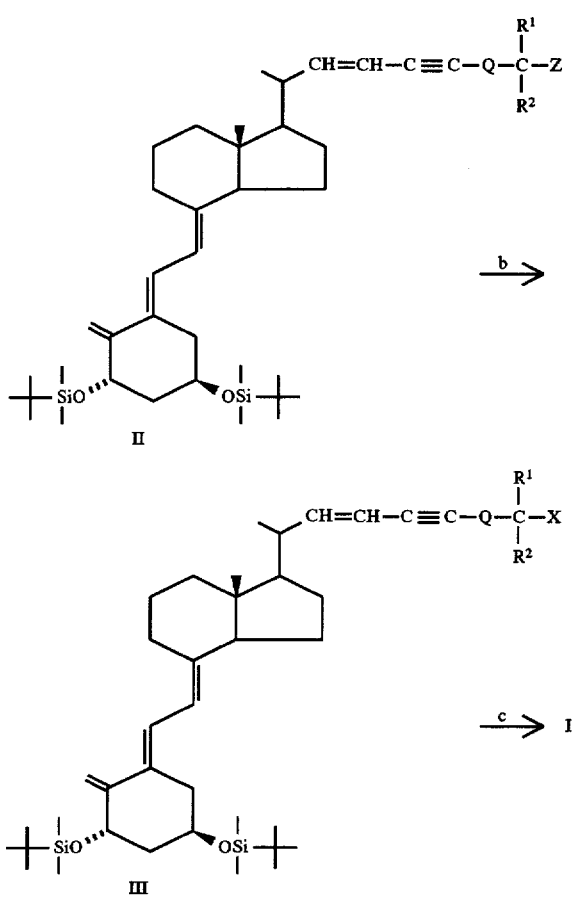

Q, R$^1$, R$^2$, Z and X are defined as above.

Notes to Scheme 1 a) Base, e.g. n-BuLi/IV (Y=(EtO)$_2$P(O) and Z=H or protected alcohol, e.g., OTHP, OTMS, OSiPh$_2$Me)/THF/ −70° to 20° C./20–200 min b) Mercury lamp/triplet sensitizer, e.g. anthracene/triethylamine/methylene chloride/10°–15° C./10–60 min c) Deprotection of all alcohol groups with e.g. "HF"/ethyl acetate/20–200 min or TBAF/THF/60° C./20–200 min and/or PPTS/EtOH/50° C./20–200 min

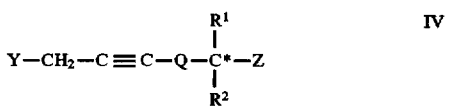

in which formula Z is hydrogen, hydroxy, trialkylsilyloxy or tetrahydro-4H-pyran-2-yloxy.

The syntheses of compounds of the general formula II and III are described in the Preparations 5–12.

The syntheses of the side chain building blocks of the general formula IV are prepared according to the methods described in Scheme 2 and in the Preparations 1–4.

Scheme 2
Synthesis of side chain building blocks of formula IV

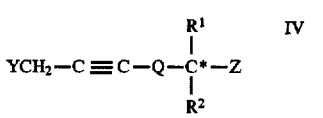

| Y | Z |
|---|---|
| HO | OH or H |
| ↓ a | |
| TsO | OH or H |
| ↓ b | |
| TsO | Protected alcohol or H |
| ↓ c | |
| Br | Protected alcohol or H |
| ↓ d | |
| (EtO)$_2$P(O) | Protected alcohol or H |

Q, R$^1$, R$^2$ and Z are defined as above.

Notes to Scheme 2 a) TsCl/base, e.g. KOE or pyridine/ether or dichloromethane/0°–25° C./0.5–5 h b) For Z=OH: 3,4-Dihydro-2H-pyran/PPTS/dichloromethane/r.t./2–20 h or trialkylsilyl chloride/base, triethylamine/THF/r.t./1–24 h c) Sodium bromide/DMF/r.t./1–10 h d) Triethyl phosphite/110°–150° C./0.4–4 h Syntheses of propargylic alcohols with the general formula IV (Y=OH and Z=OH or H) are described in the chemical literature (e.g. McLamore, W. M. et al., J. Org. Chem., 19, 570–574 (1954); Gouge, M., Ann. Chim., 6, 648–702 (1951); Colonge, J., Bull. Soc. Chim. Fr., 1959, 408–412) and/or is known to a person skilled in the art.

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient (s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100 µ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and fluorinated $C_1$–$C_6$-alkyl hydrocarbons are especially preferred. Generally, the propellant constitutes 45 to 99.9% w/w of the formulation whilst the active ingredient constitutes 0.1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like. The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 µg, preferably from 0.2–25 µg, of a compound of formula I are administered. In the topical treatment of dermatological disorders, ointments, creams or lotions containing from 0.1–500 µg/g, and preferably from 0.1–100 µg/g, of a compound of formula I are administered. For topical use in ophthalmology ointments, drops or gels containing from 0.1–500 µg/g, and preferably from 0.1–100 µg/g, of a compound of formula I are administered. The oral compositions are formulated, preferably as tablets, capsules, or drops, containing from 0.05–50 µg, preferably from 0.1–25 µg, of a compound of formula I, per dosage unit.

The invention will now be further described in the following non-limiting General Procedures, Preparations and Examples:

General Procedures, Preparations and Examples

The exemplified compounds I are listed in Table 1, whereas compounds of the general formula II and III are listed in Table 2.

For $^1$H nuclear magnetic resonance spectra (300 Mhz) chemical shift values (δ) are quoted, unless otherwise specified, for deuteriochloroform solutions relative to internal tetramethylsilane (δ=0.00) or chloroform (δ=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium/benzophenone. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

TABLE 1

| Comp. No. | Example No. | General formula | 20 conf. | Q | R¹ | R² | X |
|---|---|---|---|---|---|---|---|
| 101 | 1 | I | R | Single bond | Et | Et | OH |
| 102 | 2 | I | S | Single bond | Et | Et | OH |
| 103 |   | I | R | CH$_2$ | Et | Et | OH |
| 104 |   | I | S | CH$_2$ | Et | Et | OH |
| 105 |   | I | R | (CH$_2$)$_2$ | Et | Et | OH |
| 106 |   | I | S | (CH$_2$)$_2$ | Et | Et | OH |
| 107 |   | I | R | CH=CH | Et | Et | OH |
| 108 |   | I | S | CH=CH | Et | Et | OH |
| 109 |   | I | R | C≡C | Et | Et | OH |
| 110 |   | I | S | C≡C | Et | Et | OH |
| 111 | 3 | I | R | Single bond | Me | Me | OH |
| 112 | 4 | I | S | Single bond | Me | Me | OH |
| 113 |   | I | R | CH$_2$ | Me | Me | OH |
| 114 |   | I | S | CH$_2$ | Me | Me | OH |
| 115 |   | I | R | (CH$_2$)$_2$ | Me | Me | OH |
| 116 |   | I | S | (CH$_2$)$_2$ | Me | Me | OH |
| 117 |   | I | R | CH=CH | Me | Me | OH |
| 118 |   | I | S | CH=CH | Me | Me | OH |
| 119 |   | I | R | C≡C | Me | Me | OH |
| 120 |   | I | S | C≡C | Me | Me | OH |
| 121 |   | I | R | Single bond | CF$_3$ | CF$_3$ | OH |
| 122 |   | I | S | Single bond | CF$_3$ | CF$_3$ | OH |

TABLE 2

| Comp. No. | Prep. No. | General formula | 20 conf. | Q | R¹ | R² | X |
|---|---|---|---|---|---|---|---|
| 201 | 5 | II | R | Single bond | Et | Et | OH |
| 202 | 6 | II | S | Single bond | Et | Et | OH |
| 203 |   | II | R | CH$_2$ | Et | Et | OH |
| 204 |   | II | S | CH$_2$ | Et | Et | OH |
| 205 |   | II | R | (CH$_2$)$_2$ | Et | Et | OH |
| 206 |   | II | S | (CH$_2$)$_2$ | Et | Et | OH |
| 207 |   | II | R | CH=CH | Et | Et | OH |
| 208 |   | II | S | CH=CH | Et | Et | OH |
| 209 |   | II | R | C≡C | Et | Et | OH |
| 210 |   | II | S | C≡C | Et | Et | OH |
| 211 | 7 | II | R | Single bond | Me | Me | OH |
| 212 | 8 | II | S | Single bond | Me | Me | OH |
| 213 |   | II | R | CH$_2$ | Me | Me | OH |
| 214 |   | II | S | CH$_2$ | Me | Me | OH |
| 215 |   | II | R | (CH$_2$)$_2$ | Me | Me | OH |
| 216 |   | II | S | (CH$_2$)$_2$ | Me | Me | OH |
| 217 |   | II | R | CH=CH | Me | Me | OH |
| 218 |   | II | S | CH=CH | Me | Me | OH |
| 219 |   | II | R | C≡C | Me | Me | OH |
| 220 |   | II | S | C≡C | Me | Me | OH |
| 221 |   | II | R | Single bond | CF$_3$ | CF$_3$ | OH |
| 222 |   | II | S | Single bond | CF$_3$ | CF$_3$ | OH |
| 301 | 9 | III | R | Single bond | Et | Et | OH |
| 302 | 10 | III | S | Single bond | Et | Et | OH |
| 303 |   | III | R | CH$_2$ | Et | Et | OH |
| 304 |   | III | S | CH$_2$ | Et | Et | OH |
| 305 |   | III | R | (CH$_2$)$_2$ | Et | Et | OH |
| 306 |   | III | S | (CH$_2$)$_2$ | Et | Et | OH |
| 307 |   | III | R | CH=CH | Et | Et | OH |
| 308 |   | III | S | CH=CH | Et | Et | OH |
| 309 |   | III | R | C≡C | Et | Et | OH |
| 310 |   | III | S | C≡C | Et | Et | OH |
| 311 | 11 | III | R | Single bond | Me | Me | OH |
| 312 | 12 | III | S | Single bond | Me | Me | OH |
| 313 |   | III | R | CH$_2$ | Me | Me | OH |
| 314 |   | III | S | CH$_2$ | Me | Me | OH |
| 315 |   | III | R | (CH$_2$)$_2$ | Me | Me | OH |
| 316 |   | III | S | (CH$_2$)$_2$ | Me | Me | OH |
| 317 |   | III | R | CH=CH | Me | Me | OH |
| 318 |   | III | S | CH=CH | Me | Me | OH |
| 319 |   | III | R | C≡C | Me | Me | OH |
| 320 |   | III | S | C≡C | Me | Me | OH |
| 321 |   | III | R | Single bond | CF$_3$ | CF$_3$ | OH |
| 322 |   | III | S | Single bond | CF$_3$ | CF$_3$ | OH |

General Procedure 1:

Condensation of Compound 1 or 2 with a compound of the general formula IV (Y=(EtO)$_2$P(O) and Z=H or protected alcohol, e.g., OTHP, OTMS, OSiPh$_2$Me) to compounds of the general formula II Compound 1 or 2 (0.5 g) and a compound of the general formula IV was dissolved in THF (15 ml) and cooled to −70° C. n-Butyl lithium (0.6 ml, 1.5M in hexane) was added and the mixture was stirred for 15 min at −70° C. followed by warming to r.t. Stirring was continued for 1.5 h. Work-up with chromatography gave a compound of the general formula II.

General Procedure 2:

Isomerization of compounds of the general formula II to compounds of the general formula III A solution of a compound of the general formula II (0.1 mmol), anthracene (0.2 mmol) and triethylamine (0.05 ml) in dichloromethane (4.0 ml) under argon in a Pyrex flask was irradiated with UV-light from a high pressure ultraviolet lamp, type TQ760Z2 (Hanau) at ca. 10° C. for 20 min under stirring. The reaction mixture was concentrated in vacuo and treated with pet.ether (2×5 ml). After filtering the filtrate was concentrated in vacuo and purified by chromatography (mixture of dichloromethane and pet.ether as eluant) to yield the title compound.

General Procedure 3:

Deprotection of compounds with the general formula III to the corresponding compounds I by treatment with "HF"

To a solution of a compound with the general formula III (0.05 mmol) in ethyl acetate (0.25 ml) was added acetonitrile (1.0 ml) followed by a 5% solution of hydrofluoric acid in acetonitrile:water, 7:1 (0.8 ml) under argon and with stirring. Stirring was continued for 45 min at ambient temperature. Saturated aqueous sodium hydrogencarbonate (10 ml) was added, and the reaction mixture was worked up (ethyl acetate). The residue was purified by chromatography (ethyl acetate or a mixture of ethyl acetate and hexane or pentate as eluant) to yield the title compound.

General Procedure 4:

Deprotection of compounds of the general formula III to the corresponding compounds I by treatment with tetra-n-butylammonium fluoride To a solution of a compound of the general formula III (0.16 mmol) in THF (5 ml), a solution of TBAF (300 mg) in THF (5 ml) was added while stirring at 60° C. under argon. Stirring was continued for one hour at 60° C., the reaction mixture was washed with saturated aqueous sodium hydrogencarbonate and worked up (ethyl acetate ). The residue was purified by chromatography (0% to 50% pet.ether in ethyl acetate as eluant) to yield the title compound.

General Procedure 5:

Deprotection of compounds with the general formula III to the corresponding compounds I by treatment with pyridinium toluene-4-sulfonate PPTS (2 mg) was added to a solution of a compound with the general formula III (0.16 mmol) in 99% ethanol (2 ml), and the mixture was stirred at 50° C. under argon for one hour. The mixture was washed with saturated aqueous sodium hydrogencarbonate and worked up (ethyl acetate).

The crude product was purified by chromatography (0% to 50% pet.ether in ethyl acetate as eluant) to give the title compound.

Preparation 1:

3-Ethyl-6-(4-toluenesulfonyloxy)-hex-4-yn-3-ol, Compound 401

An ice-cold solution of 4-toluenesulfonyl chloride (6.4 g) and 4-ethylhex-2-yn-1,4-diol (McLamore, W. M. et al., J. Org. Chem., 19, 570–574 (1954) and Gouge, M., Ann. Chim., 6, 648–702 (1951)) (4.0 g) in ether (40 ml) was stirred with powdered potassium hydroxide (15 g) for 2 h. Water was added and the mixture was extracted with ether (2×250 ml). Work-up with chromatography using ether/pentane 1:1 (v/v) gave the title compound (6.5 g). $^1$H NMR: 0.91 (t, 6H), 1.55 (q, 4H), 1.83 (s, 1H), 2.45 (s, 2H), 4.76 (s, 2H), 7.36 (d, 2H), 7.82 (d, 2H).

Preparation 2:

4-Ethyl-4-(tetrahydro-4H-pyran-2-yloxy)-1-(4-toluensulfonyloxy)hex-2-yne, Compound 402

A solution of Compound 401 (6.5 g), PPTS (0.73 g) and 3,4-dihydro-2H-pyran (2 g) in dichloromethane (33 ml) was stirred at r.t. for 17 h. Dichloromethane (250 ml) was added and the solution was washed with brine (250 ml). Work-up with chromatography with ether/pentane 1:1 (v/v) gave the title compound (7.1 g). $^1$H NMR: 0.85 (t, 6H), 1.55 (q, 4H), 1.42–1.90 (m, 6H), 2.45 (s, 3H), 3.47 (m, 1H), 3.89 (m, 1H), 4.79 (s, 2H), 4.85 (m, 1H), 7.35 (d, 2H), 7.82 (d, 2H).

Preparation 3:

1-Bromo-4-ethyl-4-(tetrahydro-4H-pyran-2-yloxy)hex-2-yne, Compound 403

A mixture of Compound 402 (7.0 g) and sodium bromide (7.0 g) in DMF (50 ml) was stirred at r.t. for 4 h. Ether (300 ml) was added and the mixture was worked up with chromatography with ether/pentane 1:1 (v/v) as eluent to give the title compound (3.9 g). $^1$H NMR: 0.96 (t, 3H), 0.96 (t, 3H) 1.45–1.90 (m, 10E), 3.51 (m, 1H), 3.95 (m, 1H), 3.98 (s, 2H), 5.00 (m, 1H).

Preparation 4:

Diethyl 4-ethyl-4-(tetrahydro-4H-pyran-2-yloxy)hex-2-yn-1-ylphosphonate, Compound 404

A mixture of Compound 403 (2.0 g) and triethyl phosphite (4.2 ml) was heated to 130° C. for 1.5 h. Excess triethyl phosphite was removed in vacuo (oil pump) for 2 h to give the title compound (2.2 g). $^1$H NMR: 0.96 (m, 6H), 1.35 (t, 6H), 1.45–1.95 (m, 10H), 2.81 (d, J=21.7 Hz, 2H), 3.50 (m, 1H), 3.93 (m, 1H), 4.18 (m, 4H), 5.05 (m, 1H).

Preparation 5: Compound 201

General Procedure 1; Compound 1.

Starting compound IV: Compound 404.

Chromatography eluant: Ether/pentane 1: 3 (v/v) .

$^1$H NMR: 0.05 (m, 12H), 0.56 (s, 3H), 0.85 (s, 9H), 0.89 (s, 9H), 0.94 (t, 6H), 1.05 (d, 3H), 1.10–2.25 (m, 24H), 2.30 (bd, 1H), 2.55 (dd, 1.H), 2.87 (bd, 1H), 3.48 (m, 1H), 3.93 (m, 1H), 4.21 (m, 1H), 4.52 (m, 1H), 4.93 (m, 1H), 4.98 (m, 1H), 5.05 (m, 1H), 5.44 (d, J=15.8 Hz, 1 H), 5.82 (d, 1H), 5.99 (dd, J=15.8 Hz and J=8.8 Hz, 1H), 6.44 (d, 1H).

Preparation 6: Compound 202

General Procedure 1; Compound 2.

Starting compound IV: Compound 404.

Chromatography eluant: Dichloromethane/pentane 2:1 (v/v).

$^1$H NMR: 0.06 (m, 12H), 0.50 (s, 3H), 0.85 (s, 9H), 0.89 (s, 9H), 0.82–1.00 (m, 9H), 1.00–2.20 (m, 24H), 2.30 (bd, 1H), 2.55 (dd, 1H), 2.86 (bd, 1H), 3.46 (m, 1H), 3.94 (m, 1H), 4.21 (m, 1H), 4.52 (m, 1H), 4.93 (m, 1H), 4.98 (m, 1H), 5.01 (m, 1H), 5.43 (d, J=15.9 Hz, 1H), 5.81 (d, 1H), 5.98 (dd, J=15.9 Hz and J=9.6 Hz, 1H), 6.44 (d, 1H).

Preparation 7: Compound 211

General Procedure 1: Compound 1.

Starting compound II: Diethyl 4-methyl-4-(tetrahydro-4H-pyran-2-yloxy)pent-2-yn-1-ylphosphonate, prepared from 4-methyl-pent-2-yne-1,4-diol (Gouge, M., Ann. Chim., 6, 648–702 (1951)) as depicted in Scheme 2.

Chromatography eluant: Ether/pentane 1:10 (v/v).

Preparation 8: Compound 212

General Procedure 1; Compound 2.

Starting compound II: Diethyl 4-methyl-4-(tetrahydro-4H-pyran-2-yloxy)pent-2-yn-1-ylphosphonate (see Preparation 7).

Chromatography eluant: Ether/pentane 1:10 (v/v).

Preparation 9: Compound 301

General Procedure 2.

Starting compound II: Compound 201.

Chromatography eluant: Ether/pentane 1: 10 (v/v).

$^1$N NMR: 0.05 (m, 12H), 0.54 (s, 3M), 0.86 (s, 18H), 0.95 (m, 6H), 1.05 (d, 3H), 1.08–2.25 (m, 25H), 2.43 (dd, 1H), 2.82 (bd, 1H), 3.48 (m, 1H), 3.91 (m, 1H), 4.18 (m, 1H), 4.34 (m, 1H), 4.85 (m, 1H), 5.03 (m, 1H), 5.17 (m, 1H), 5.43 (d, J=15.8 Hz, 1H), 5.99 (dd, J=15.8 Hz and J=8.7 Hz, 1H), 6.00 (d, 1H), 6.44 (d, 1H).

Preparation 10: Compound 302

General Procedure 2.

Starting compound II: Compound 202.

Chromatography eluant: Dichloromethane/pentane 4:1 (v/v).

$^1$H NMR: 0.05 (m, 12H), 0.49 (s, 3H), 0.86 (s, 18H), 0.75–2.00 (m, 32H), 2.11 (m, 1H), 2.20 (dd, 1H), 2.44 (dd, 1H), 2.81 (bd, 1H), 3.47 (m, 1H), 3.95 (m, 1H), 4.18 (m, 1H), 4.36 (m, 1H), 4.85 (m, 1H), 5.01 (m, 1H), 5.17 (m, 1H), 5.43 (d, J=15.9 Hz, 1H), 5.97 (dd, J=15.9 Hz and J=9.6 Hz, 1H), 6.00 (d, 1H), 6.22 (d, 1H).

Preparation 11: Compound 311

General Procedure 2.

Starting compound II: Compound 211.

Chromatography eluant: Dichloromethane/pentane 4:1 (v/v).

Preparation 12: Compound 312

General Procedure 2.

Starting compound II: Compound 212.

Chromatography eluant: Dichloromethane/pentane 4:1 (v/v).

EXAMPLE 1:

1(S),3(R)-Dihydroxy-20(R)-(5-ethyl-5-hydroxy-hept-1(E)-en-3-yn-1-yl)-9,10-seco-pregna-5(Z),7(E),10(19)-triene (Compound 101)

Method: General Procedure 3.

Starting material: Compound 301.

Chromatography. eluant: Ethyl acetate.

$^1$H NMR: 0.56 (s, 3H), 1.03 (t, 6H), 1.05 (d, 3H), 1.15–2.25 (m, 21H), 2.31 (dd, 1H), 2.60 (m, 1H), 2.83 (m, 1H), 4.23 (m, 1H), 4.43 (m, 1H), 5.00 (m, 1H), 5.33 (m, 1H), 5.43 (d, J=15.8 Hz, 1H), 5.99 (dd, J=15.8 Hz and 8.8 Hz, 1H), 6.01 (d, 1H), 6.37 (d, 1H).

EXAMPLE 2:

1(S),3(R)-Dihydroxy-20(S)-(5-ethyl-5-hydroxy-hept-1(E)-en-3-yn-1-yl)-9,10-seco-pregna-5(Z),7(E),10(19)-triene (Compound 102)

Method: General Procedure 3.

Starting material: Compound 302.

Chromatography eluant: Ethyl acetate.

$^1$H NMR: 0.50 (s, 3H), 0.95 (d, 3H), 1.03 (t, 6H), 1.10–2.25 (m, 21H), 2.31 (dd, 1H), 2.60 (m, 1H), 2.83 (dd, 1H), 4.23 (m, 1H), 4.43 (m, 1H), 5.00 (m, 1H), 5.28 (m, 1H), 5.42 (d, J=15.9 Hz, 1H), 5.98 (dd, J=15.9 Hz and 9.7 Hz, 1H), 6.01 (d, 1H), 6.37 (d, 1H).

EXAMPLE 3:

1(S),3(R)-Dihydroxy-20(R)-(5-methyl-5-hydroxy-hex-1(E)-en-3-yn-1-yl)-9,10-seco-pregna-5(Z),7(E),-10(19)-triene (Compound 111)

Method: General Procedure 3.

Starting material: Compound 311.

Chromatography eluant: Ethyl acetate.

EXAMPLE 4:

1(S),3(R)-Dihydroxy-20(S)-(5-methyl-5-hydroxy-hex-1(E)-en-3-yn-1-yl)-9,10-seco-pregna-5(Z),7(E),10(19)-triene (Compound 112)

Method: General Procedure 3.

Starting material: Compound 312.

Chromatography eluant: Ethyl acetate.

EXAMPLE 5:

Capsules containing Compound 101

Compound 101 was dissolved in arachis oil to a final concentration of 1 μg/ml oil. Ten parts by weight of gelatine, 5 parts by weight of glycerin, 0.08 parts by weight potassium sorbate, and 14 parts by weight distilled water were mixed together with heating and formed into soft gelatine capsules. These were then filled each with 100 μl of the oily solution of Compound 101.

EXAMPLE 6:

Dermatological Cream containing Compound 101

Compound 101 (0.05 mg) was dissolved in almond oil (1 g). To this solution was added mineral oil (40 g) and self-emulsifying beeswax (20 g). The mixture was heated to liquifidation. After the addition of hot water (40 ml), the mixture was mixed well. The resulting cream contains approximately 0.5 μg of compound 101 per gram of cream.

What I claim is:

1. A compound of the formula I

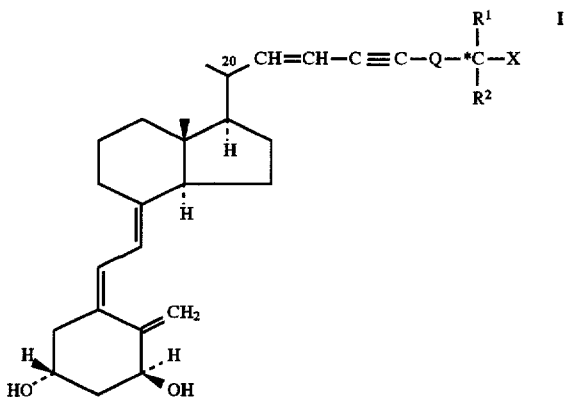

in which formula X is hydrogen or hydroxy; $R^1$ and $R^2$ which may be the same or different, stand for hydrogen or $C_1$–$C_4$ hydrocarbyl; or $R^1$ and $R^2$ taken together with the carbon atom bearing the group X, can form a $C_3$–$C_8$ carbocyclic ring; Q is a single bond ; $R^1$, $R^2$ and/or Q may be optionally substituted with one or more fluorine atoms; and prodrugs of I in which one or more of the hydroxy groups are masked as groups which can be reconverted to hydroxy groups in vivo.

2. A compound of formula I according to claim 1 in which Q is a single bond.

3. A compound of formula I according to claim 1 in which X is hydroxy.

4. A stereoisomer of a compound according to claim 1 in pure form or a mixture of such stereoisomers.

5. A compound according to claim 1 which is 1(S),3(R)-dihydroxy-20(R)-(5-ethyl-5-hydroxy-hept-1(E)-en-3-yn-1-yl)-9,10-seco-pregna-5(Z),7(E),10(19)-triene.

6. A method for producing a compound of formula I of claim 1 which comprises reacting 1(S),3(R)-bis-(tert-butyldimethylsilyloxy)-20(R or S)-formyl-9,10-seco-pregna-5(E),7(E),10(19)-triene with a compound of the general formula IV

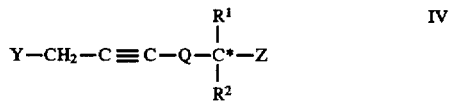

in tetrahydrofuran in the presence of a strong base at −70° to 20° C. for 10 to 100 min to produce a compound of the general formula II;

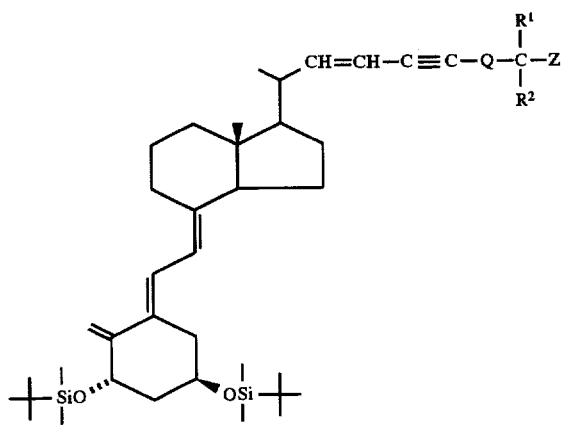

in which formulae Y is (EtO$_2$P(O) and Z is H or protected alcohol and Q, R$^1$ and R$^2$ are defined as in claim 1; and then subjecting the compound of the general formula II to a triplet-sensitized 5E to 5Z photoisomerization followed by desilylation with a member of the group consisting of hydrofluoric acid, tetra-n-butylammonium fluoride and pyridinium para-toluenesulfonate to form the compound of formula I.

7. A pharmaceutical composition containing an effective amount of one or more of the compounds of claim 1, together with pharmaceutically acceptable, non-toxic carrier.

8. A pharmaceutical composition according to claim 7 in dosage unit form containing from 0.1 ppm to 0.1% by weight of the dosage unit of a compound of formula I.

9. A method for the treatment of hyperparathyroidism and autoimmune diseases, hypertension, acne, alopecia, skin ageing, imbalance in the immune system, inflammatory diseases, diseases characterized by abnormal cell differentiation and/or cell proliferation or steroid induced skin atrophy, for promotion of osteogenesis and for the treatment of osteoporosis, consisting in administering to a patient in need thereof an effective amount of a pharmaceutical composition according to claim 7.

* * * * *